(12) United States Patent
Naik et al.

(10) Patent No.: US 8,234,127 B2
(45) Date of Patent: Jul. 31, 2012

(54) PERSONALIZED HEALTHCARE MANAGEMENT SYSTEM

(75) Inventors: Praful Ramachandra Naik, Honavar (IN); Mohan Harakchand Bhandari, Pune (IN)

(73) Assignee: Bilcare Limited (IN)

( * ) Notice: Subject to any disclaimer, the term of this patent is extended or adjusted under 35 U.S.C. 154(b) by 351 days.

(21) Appl. No.: 12/528,058

(22) PCT Filed: Dec. 13, 2007

(86) PCT No.: PCT/IN2007/000590
§ 371 (c)(1),
(2), (4) Date: Oct. 19, 2009

(87) PCT Pub. No.: WO2008/102370
PCT Pub. Date: Aug. 28, 2008

(65) Prior Publication Data
US 2010/0036681 A1    Feb. 11, 2010

(30) Foreign Application Priority Data

Feb. 21, 2007   (IN) .......................... 350/MUM/2007

(51) Int. Cl.
*G06Q 10/00* (2012.01)
(52) U.S. Cl. ..................................... 705/2; 705/3; 705/4
(58) Field of Classification Search .................. 705/2–3
See application file for complete search history.

(56) References Cited

U.S. PATENT DOCUMENTS

| | | | |
|---|---|---|---|
| 5,960,403 A * | 9/1999 | Brown | 705/2 |
| 5,991,731 A * | 11/1999 | Colon et al. | 705/3 |
| 7,054,823 B1 * | 5/2006 | Briegs et al. | 705/2 |
| 7,624,028 B1 * | 11/2009 | Brown | 705/3 |
| 7,761,312 B2 * | 7/2010 | Brown | 705/3 |
| 7,827,040 B2 * | 11/2010 | Brown | 705/2 |
| 7,853,455 B2 * | 12/2010 | Brown | 705/2 |
| 2003/0063524 A1 * | 4/2003 | Niemiec et al. | 368/10 |
| 2003/0110060 A1 | 6/2003 | Clementi | |
| 2006/0058724 A1 | 3/2006 | Handfield et al. | |
| 2006/0065670 A1 | 3/2006 | Doublet et al. | |
| 2007/0016443 A1 | 1/2007 | Wachman et al. | |

OTHER PUBLICATIONS

PCT Notification of Transmittal of International Preliminary Report on Patentability, PCT Application No. IN 2007/00059 dated May 11, 2009.
PCT International Search Report, PCT Application No. IN 2007/00059 dated Aug. 29, 2008.
Extended European Search Report for EP 07870549 dated Oct. 7, 2011.

* cited by examiner

*Primary Examiner* — Robert Morgan
*Assistant Examiner* — Michael Fuelling
(74) *Attorney, Agent, or Firm* — Cook Alex Ltd.

(57) ABSTRACT

Personalized healthcare management system. The personalized integrated healthcare anti-counterfeit management system provides pack authentication, user (5) feedback and compliance, documentation of the dosage uptake by the users (5), maintenance of user (5) related data and displaying compliance and feedback information, and liaising with healthcare agencies, users' nominated persons and/or medical practitioners (6). It further provides real-time and authentic data in raw and analysed form to diverse agencies in the healthcare chain. Moreover, a method for delivering pharmacovigilance related information in clinical trials is disclosed. Authentication of diverse healthcare agencies in the healthcare value chain such as medical practitioners (6), users (5), pharmacists (7), pharmaceutical companies (9), and clinical researchers is taken care of.

15 Claims, 8 Drawing Sheets

Figure 2:
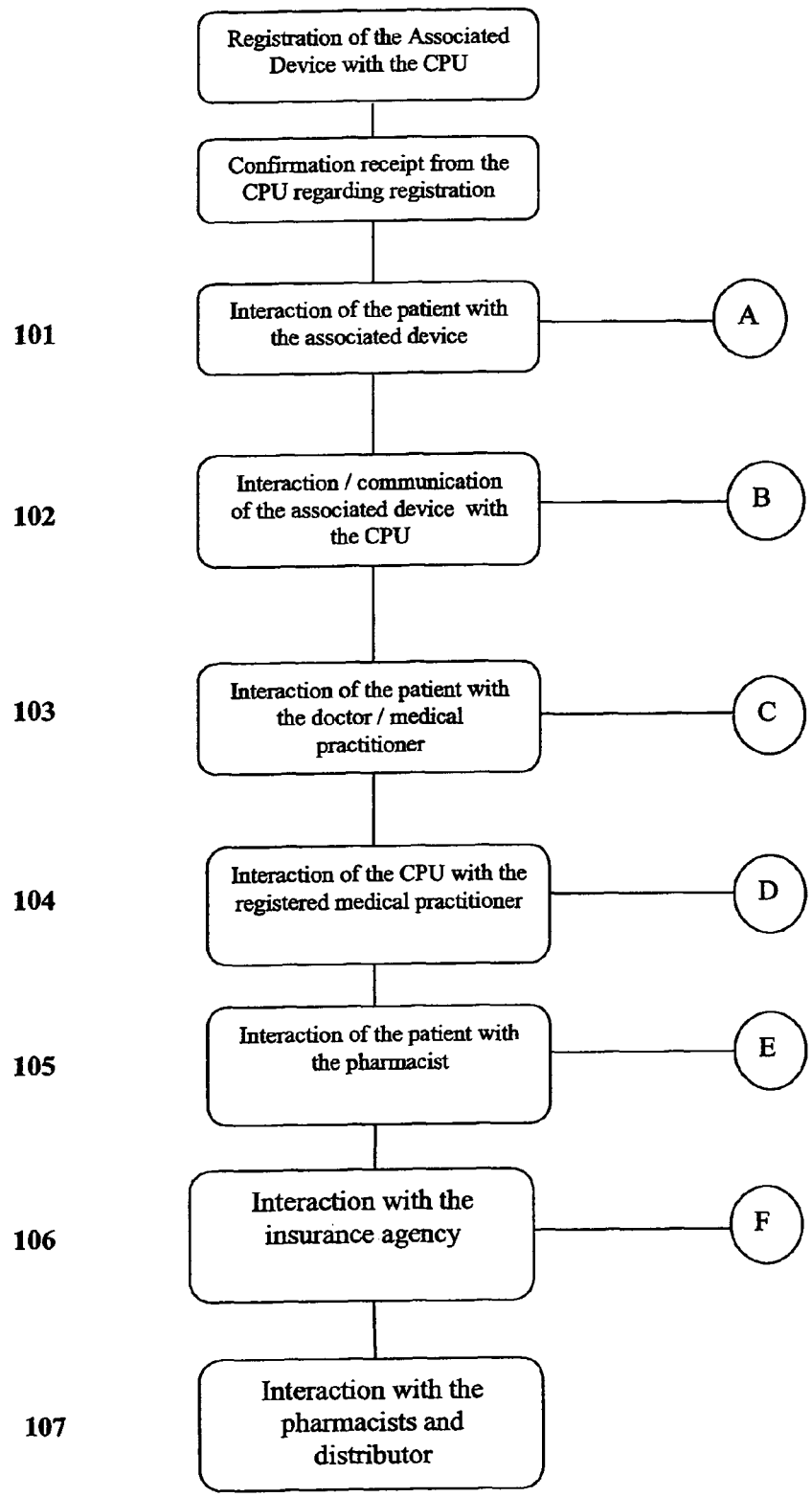

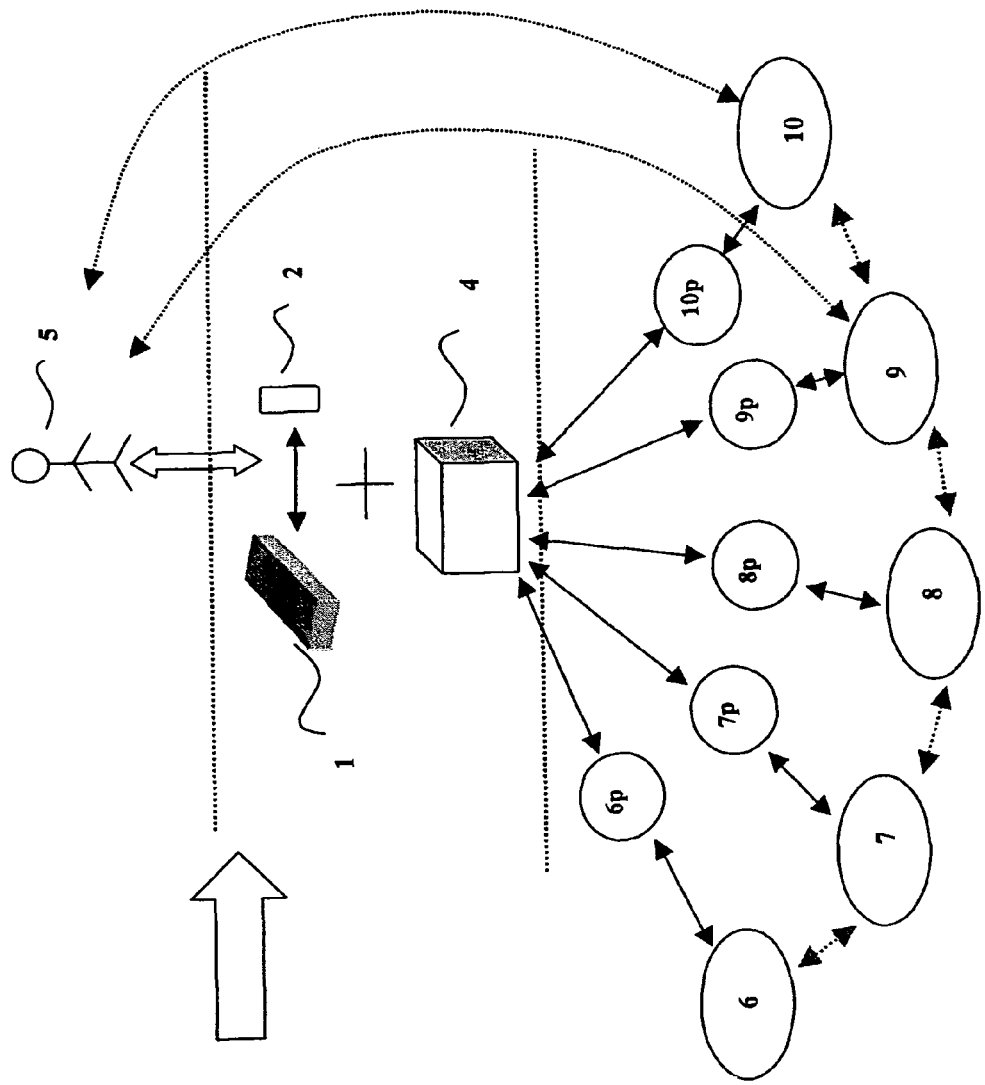
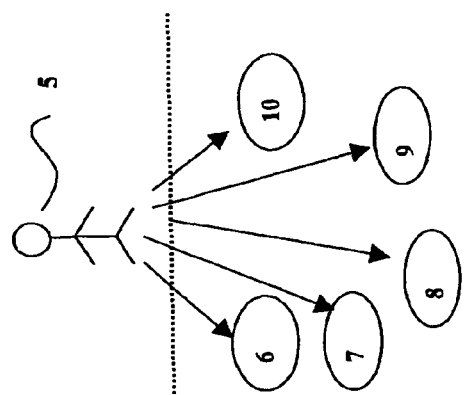
Figure 1 (a)
Figure 1 (b)

PERSONALIZED HEALTHCARE MANAGEMENT SYSTEM

This is a National Stage of PCT Application No. PCT/IN2007/000590, which was filed on Dec. 13, 2007 and claims priority to Indian Application No. 350/MUM/2007, which was filed on Feb. 21, 2007, both of which are incorporated by reference.

FIELD OF THE INVENTION

The present invention relates to a personalized integrated healthcare anticounterfeit management system providing pack authentication, user feedback and compliance, documentation of the dosage uptake by the users, maintenance of user related data and displaying compliance and feedback information, liaising with the healthcare agencies, users' nominated persons/medical practitioner, providing real-time and authentic data in raw and analysed form to diverse agencies in the healthcare chain.

BACKGROUND ART

The health care sector is becoming increasingly demanding. The ultimate end user drug consumer that is patient is the focal point/hub in the healthcare system. At the same time related entities such as doctors, pharmacies, insurance agency, pharmaceutical company, distributor etc. form important links/stakeholders and are integral part of the healthcare circle and their cognitive effort plays vital role in maintaining patients healthcare and providing value added services to him/her. Conventionally, these links are isolated and not integrated with the patient to understand his/her usage pattern of drug and related feedback. Further patient compliance and feedback plays a significant role in clinical research/trials as they provide insight by way of pharmacovigilance into the drug/medicine under development.

If these entities appropriately and authentically liaison with patient and work in tandem with the information generated by and from the patients end using means to link the patient and his/her compliance process such as his compliance with drug schedule, feedback about symptoms etc., synergistic effect could be produced resulting in patient compliance thereby enhancing quality of health care and providing value addition to all the links in this healthcare system. Various healthcare management systems are reported in the literature. They are as follows:

U.S. Pat. No. 6,961,285 discloses a system and process for assisting patients in taking medication and assisting third parties in accumulating information regarding patient medication intake. The instrumented medication package along with a portable medication package is communicably connected to the third parties via computer network. However, the process is restricted to only accumulating and transmitting data related to patient medication intake. However the system is not capable of integrated value added functionalities of product authentication, patient feedback, pharmacovigilance, etc.

U.S. Pat. No. 5,781,442 discloses patient management system capable of monitoring, controlling and tracking the administration of care in a health care institution. The invention provides a modular management system that processes the functional information from the hospital and its administration such as patient list and their data, ongoing procedures. This system is restricted to management of health care within an institution/hospital. Further the management system does not facilitate product authentication, online feedback of the patients with doctor, pharmacies, insurance agency, pharmaceutical company etc.

U.S. Pat. No. 6,021,392 discloses a system and method for drug and health care supply distribution and replenishment wherein a Health care provider/hospital having a, drug dispensing machine/hand held drug dispensing unit and second computer located at a drug supplier facility are in electronic communication with each other providing records of drugs received by the health care provider, drugs dispensed to patients at the health care provider, and an ongoing inventory of drugs stored at the health care provider. This inventory system is not capable of authenticating the drugs, or online record patient feedback, or network with value added services to doctors, pharmacies, insurance agency, pharmaceutical company etc at it is merely manages the drug inventory control.

The U.S. Pat. No. 5,390,238 discloses health care support method and system for health care support. The system comprises of health support unit for monitoring and supporting a patient monitoring terminal, and a network server coupled between the health support unit and monitoring terminal for exchanging information between health support units and monitoring terminal. The method comprises the steps of:

inputting a medication delivery schedule to the health support unit, synthesizing speech in the health support unit to inquire a wellness status of the patient at predetermined intervals and to remind the patient to take medication as scheduled, recognizing patient speech in the health support unit, recording patient data concerning the patient's compliance with the medication delivery schedule and the patient's wellness check results, transmitting patient data to a central network server for access by the patient's health care provider.

However the system and the method disclosed is limited to monitoring the patients compliance with medication delivery schedule. Further it does not provide facility and method of liaison/interaction with the other entities in the health care circle such as doctors, pharmacies, insurance agency, pharmaceutical company, distributor etc.

U.S. Pat. No. 5,558,638 discloses a system for monitoring the health and medical requirements of plurality of patents at remote sites and providing these requirements to a care center. The system comprises a sensor for monitoring the patient's medical state, the sensor generating a parameter indicative of the patient's medical state; a data base located at a remote location from the sensor for storing the patient's medical state; a means for communicating the parameter to the data base; a means for retrieving the parameter from the data base; and a means for providing medical procedure to the patient in response to the retrieved parameter. It may be noted that this system allows for the collection of information from the patient through sensors on the patients and does not procure personal feedback from the patient nor does the system authenticate the drug being taken by the patient. Further this is not a system capable of. comprehensively managing a distributed healthcare system by integrating several of all the stake holders of a healthcare system.

U.S. Pat. No. 7,251,609 discloses a method for conducting clinical trials over the internet. The invention encompasses a method of conducting a clinical trial of a test substance from a primary site, via the internet The internet is used in various phases of a clinical trial, including: recruiting and screening for candidates who are eligible to participate in a clinical trial of a test substance using the internet; obtaining, directly from a participant at a remote site, personal information as well as information allowing a determination of any effect(s) of the test substance on the participant after use (e.g., by evaluation forms completed and transmitted over the internet); compiling data from multiple participants. This system does not procure personal feedback from the patient when he has consumed the medicine nor does the system authenticate the pack with the protocol being taken by the patient during a clinical trial. Further this is not a system capable of comprehensively managing a distributed healthcare system by integrating several of all the stakeholders of a healthcare system.

U.S. Pat. No. 5,778,882 discloses a health monitoring system which tracks the state of health of a patient and compiles a chronological health history of the patient uses a multiparametric monitor which periodically and automatically measures and records a plurality of physiological data from sensors in contact with the patients body. The data provides the information necessary to derive patterns, which are characteristic of healthy patients as well as those who are ill. The data collected is periodically uploaded to a database in which it is stored along with similar health histories for other patients. The, monitor is preferably self-contained in a chest strap, which is located on the patients torso, and makes use of a controller, which controls sampling of the desired data and storage of the data to a local memory device pending uploading to the database. Such a system allows for the collection, storage and retrieval of information from the patient via a chest strap on the patients. It does not procure online personal feedback from the patient nor does the system authenticate the pack with the protocol being taken by the patient in a normal course of treatment of during a clinical trial. Further this is not a system capable of comprehensively managing a distributed healthcare system by integrating several of all the stakeholders of a healthcare system.

U.S. Pat. No. 6,440,069 discloses Health monitoring system that monitors the health of a patient includes an ingestible capsule containing a medication to be consumed by a subject. A signal generator located within the capsule outputs an electrical signal having a predetermined characteristic indicative of said medication, said capsule and said medication being liberated by dissolution of the capsule in the stomach acid of a subject. A signal detector, preferably having an input in electrical contact with a portion of the subject's skin, is used to detect the electrical signal. This allows the ingestion of the medication to be tracked. As in the case of other prior art, it does not procure personal feedback from the patient nor does the system authenticate the pack with the protocol being taken by the patient in a normal course of treatment of during a clinical trial. Further this is not a system capable of comprehensively managing a distributed healthcare system by integrating several of all the stakeholders of a healthcare system.

Thus review of the prior art reveals following drawbacks:
The systems and methods do not address patient centric, interactive, authenticated integration of the complete cross section right from the medication package, insurance agency to pharmacists of the health care system wherein the interaction between them brings value to each of the entities and produces synergistic effect to ensure patient compliance including appropriate patient feedback from clinical trials and/or collection of pharmacovigilance data and in the process enhancing the value of the total healthcare system.
Methods and systems restricted to hospitals/health care institutions only
The information generated by the patient at his/her end, regarding drug consumption, its symptoms etc. is not been accessed/used/transmitted as a primary source to various links of the health care system.
The methods and systems do not provide the facility for patient registration and identification with the system, authentication & registration of the medication package and authentication of the facilitators such as medical practitioners, pharmacist etc. are not reported in the prior art There is a need to develop a personalized integrated healthcare anticounterfeit management method and a system thereof wherein patient is at the focal point (patient centric method) and stakeholders/healthcare agencies such as medical practitioners, health insurance agency, healthcare regulators, pharmaceutical companies, clinical researchers, pharmacies and medication package are integrated with the patient and also are in interaction/communication/liaison with each other via authenticated and registered process to provide the technical effect of user compliance to doctors prescription, recording user compliance to medication and acquiring patient feedback on the effects of the medication, maintaining data and displaying compliance and feedback information, liaising with users' nominated persons and medical practitioner, providing real-time and authentic data to insurance agencies, creating statistical and other reports which can be accessed by the healthcare agencies by means including websites/ftp sites. The present invention is also especially useful in clinical trials/research and pharmacovigilance in providing an effective and reliable way of monitoring patient compliance with a specified healthcare regime.

SUMMARY OF THE INVENTION

The main object of the invention is to provide a personalized integrated healthcare anticounterfeit management method and a system capable of pack authentication, user feedback and compliance, documentation of the dosage uptake by the users, maintenance of user related data and displaying compliance and feedback information, liaising with various healthcare agencies, users' nominated persons/ medical practitioner, providing real-time and authentic data in raw and analysed form to diverse agencies in the healthcare chain. A further object is to provide a method of providing pharmacovigilance related information in clinical trials.

Yet another object of the invention is to provide an integrated healthcare management system relating to a patient which is interactive between a first healthcare agency and at least one other party, the said other party being selected from the patient and at least one other healthcare agency.

Another object of the invention is to provide a method for authentication of medical package against counterfeit.

Yet another object of the invention is to provide a patient medication system that is communicably linkable to the healthcare agencies.

Yet another object of the invention is to provide authentication of diverse healthcare agencies in the healthcare value chain such as medical practitioners, users, pharmacists, pharmaceutical companies and clinical researchers.

Yet another object of the invention is to provide a method for user compliance of medication intake as prescribed by medical practitioner and/or clinical researcher and feed back regarding the same from/to the user.

Yet another object of the invention is to provide a method for creating a database of maintenance of user related health records/feedback and clinical trials information.

Yet another object of the invention is to provide a method for maintaining secure databases and interactions between user, the package containing the dosage, and diverse agencies in the healthcare value chain.

Thus in accordance with the invention a method of providing an integrated healthcare management system relating to a patient which is interactive between a first healthcare agency and at least one other party, the said other party being selected from the patent and at least one other healthcare agency, the system comprising:

a. registering a defined healthcare regime for the patent in a remote system and optionally other data relating directly or indirectly to the healthcare regime;
b. providing to the patent a patient medication system comprising a package comprising a product for dispensing, information relating to the identity of the package and the patient medication system being communicably linked to the remote system;
c. recording information relating to the identity of the package in the patient medication system or remote system and whereby upon dispensing of the product the said recorded information is comparable with the information of the package to determine whether or not the information of the said product dispensing system corresponds with the said recorded information;
d. providing to the at least one healthcare agency a communication port communicably linked to the remote system;
e. periodically providing information relating to the identity of the patient and/or the status of the package from the patient medication system to the remote system;
f. comparing the information periodically transmitted to the remote system with the healthcare regime recorded for the patient in the remote system to ascertain whether the information corresponds with the recorded healthcare regime;
g. optionally providing information from the remote system to the patient medication system to indicate whether the status of the patient medication system and/or identity of the patient corresponds with the information relating to the healthcare regime and/or the identity of patient;
h. providing information from the remote system to the at least one healthcare agency indicating that a periodic transmission of information has been received by the remote system;

whereby the first healthcare agency and at least one other party, the said other party being selected from the patient and at least one other healthcare agency transmit and/or receive via the remote system information relating directly or indirectly to the healthcare regime of the patient
wherein
the said integrated healthcare management system comprises of:
i) a remote system for storing a defined healthcare regime for the patient and optionally other data relating directly or indirectly to the healthcare regime;
ii) a patient medication system for use by the patient providing medication to be taken by the patient;
iii) a communication port for at least one healthcare agency to communicate interactively with the remote system;
wherein;
iv) the remote system and the patient medication system are linked and interactively communicable whereby information relating to the healthcare regime is transmissible to the patient medication system and accessible by the patient and information relating to the patient medication system is transmissible to the remote system and comparable with the defined healthcare regime stored in the system; and
v) the communication port is adapted for the at least one healthcare agency to input information and/or to receive information relating to the healthcare regime of the patient by transmission of information between the communication port and to the remote system;

the arrangement being such that the first healthcare agency and at least one other party, the said other party being selected from the patient and at least one other healthcare agency transmit and/or receive via the remote system information relating directly or indirectly to the healthcare regime of the patient including the information obtained in clinical research and pharmacovigilance;
wherein
the patient medication system comprises:
a) a package containing medication and which has information relating to the identity of the package; and
b) an associated device with which the package is engagable, the associated device being communicably linked to the remote system and registrable with the remote system;
and recording information relating to the identity of the package in the associated device or remote system whereby upon engagement of the package and associated device the said recorded information is comparable with the information of the package to determine whether or not the information of the engaged package corresponds with the said recorded information; and optionally providing information from the remote system to the associated device to indicate whether the status of the package and/or identity of the patient corresponds with the information relating to the healthcare regime and/or the identity of patient;
to facilitate authentication, compliance optionally including appropriate patient feedback from clinical trials and/or collection of pharmacovigilance data, liaising and integration of the patient with various stake holders/healthcare agencies such as medical practitioner, pharmacists, distributor, pharma company, health insurance agency, clinical researchers and their liaising with each other.

DETAILED DESCRIPTION OF THE INVENTION

The features and advantages of the present invention will become apparent in the following detailed description and the preferred embodiment with reference to the accompanying figures.

Definitions

Compliance: a patients (or doctor's) adherence to a recommended course of treatment Pharmacovigilance is the pharmacological science relating to the detection, assessment, understanding and prevention of adverse effects, particularly long term and short term side effect of medicines. Generally speaking pharmacovigilance is the science of collecting monitoring, researching, assessing and evaluating information from healthcare providers and patients on the adverse effects of medications.

comprehensive personalized healthcare anti-counterfeit management system is a personalized integrated healthcare anticounterfeit management method and a system Healthcare agencies include diverse stakeholders and facilitators such as medical practitioners, pharmacists, clinical researchers, insurance agencies, distributors and others in the healthcare system.

remote system includes devices such as servers, central processing units, communication devices.

healthcare regime means medication schedule, prescription, medication protocol including those administered in clinical trials.

patient medication system includes packages provided with package identifiers such as a blister pack with a smart chip, bottle with chip, randomized pattern etc and optionally with an associated device described herein Associated device means a device that is capable of uniquely identifying a package, sensing presence/absence of product in the package and interacting with the patient, remote system and other external devices.

Information related to identity of the package and status of the package includes information related to authentication of the medication package identify and confirm the source of the package including production batch details, and access information such as manufacturing date, expiry date, place of manufacture, geographical validation in that area;

a communication port includes Web based portals, communication means

This invention also facilitates user compliance including appropriate patient feedback which may be provided manually or automatically and is especially useful in clinical trials and/or collection of pharmacovigilance data.

The present invention is particularly useful in monitoring pharmacovigilance, providing pharmacovigilance data and may be used to monitor participant compliance with the research protocol and goals to determine preferred actions to be performed. Optionally, the invention may provide a spectrum of noncompliance, from minor noncompliance needing only corrective feedback, to significant noncompliance requiring participant removal from the clinical trial or from future clinical trials. The decision rules can also be domain-specific, such as detecting non-compliance or fraud among subjects in a drug trial, for example a cardiovascular drug trial, or demographically specific, such as taking into account gender, age or location, which provides for algorithms and decision rules to be optimized for the specific sample of participants being studied.

FIG. 1 Schematic of the system (Sheet 1)

FIG. 2 Steps of system operation (Sheet 2)

Figure 2A:
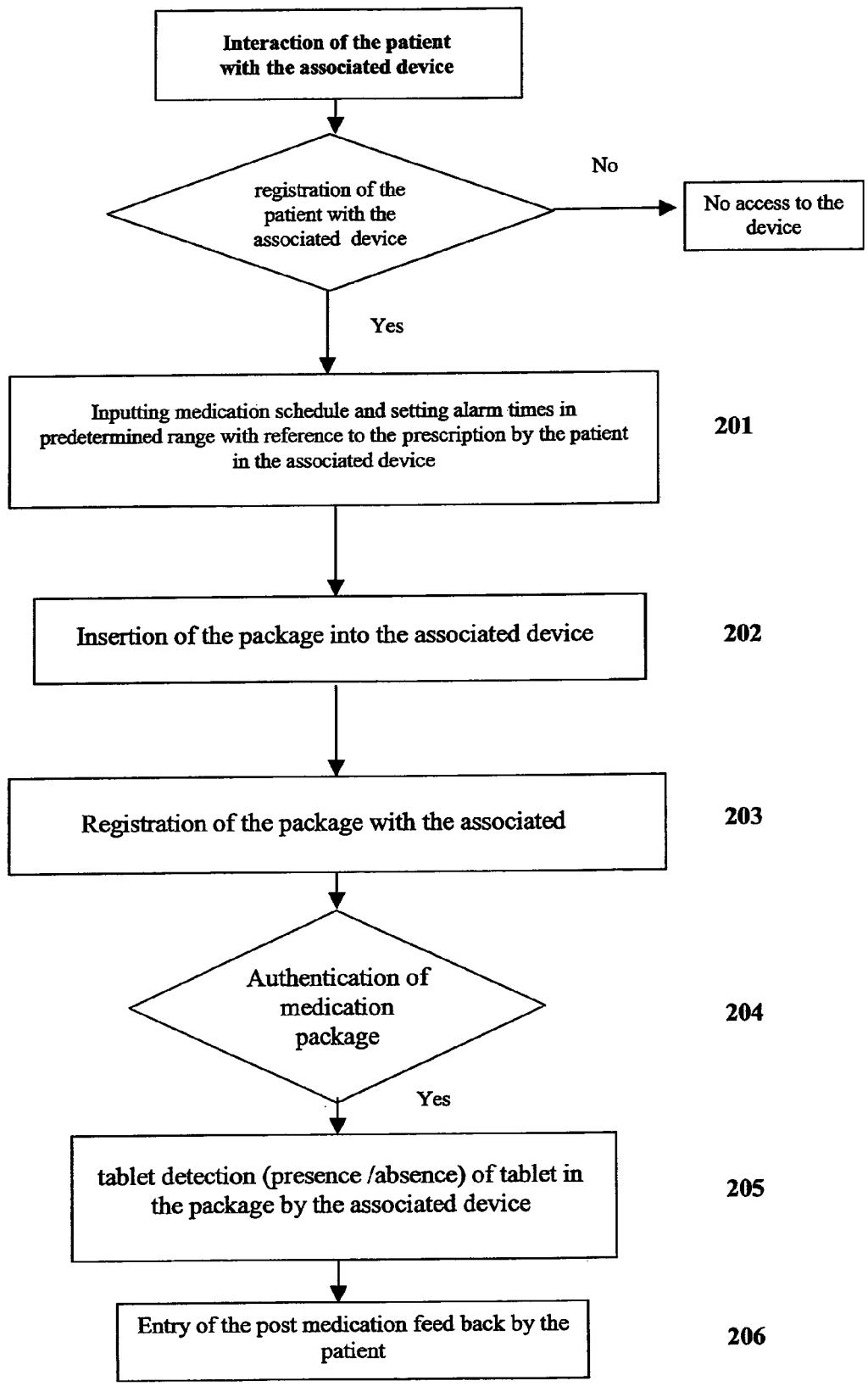

FIG. 2*a* Steps of interaction of the patient with the associated device (Sheet 3)

Figure 2B:
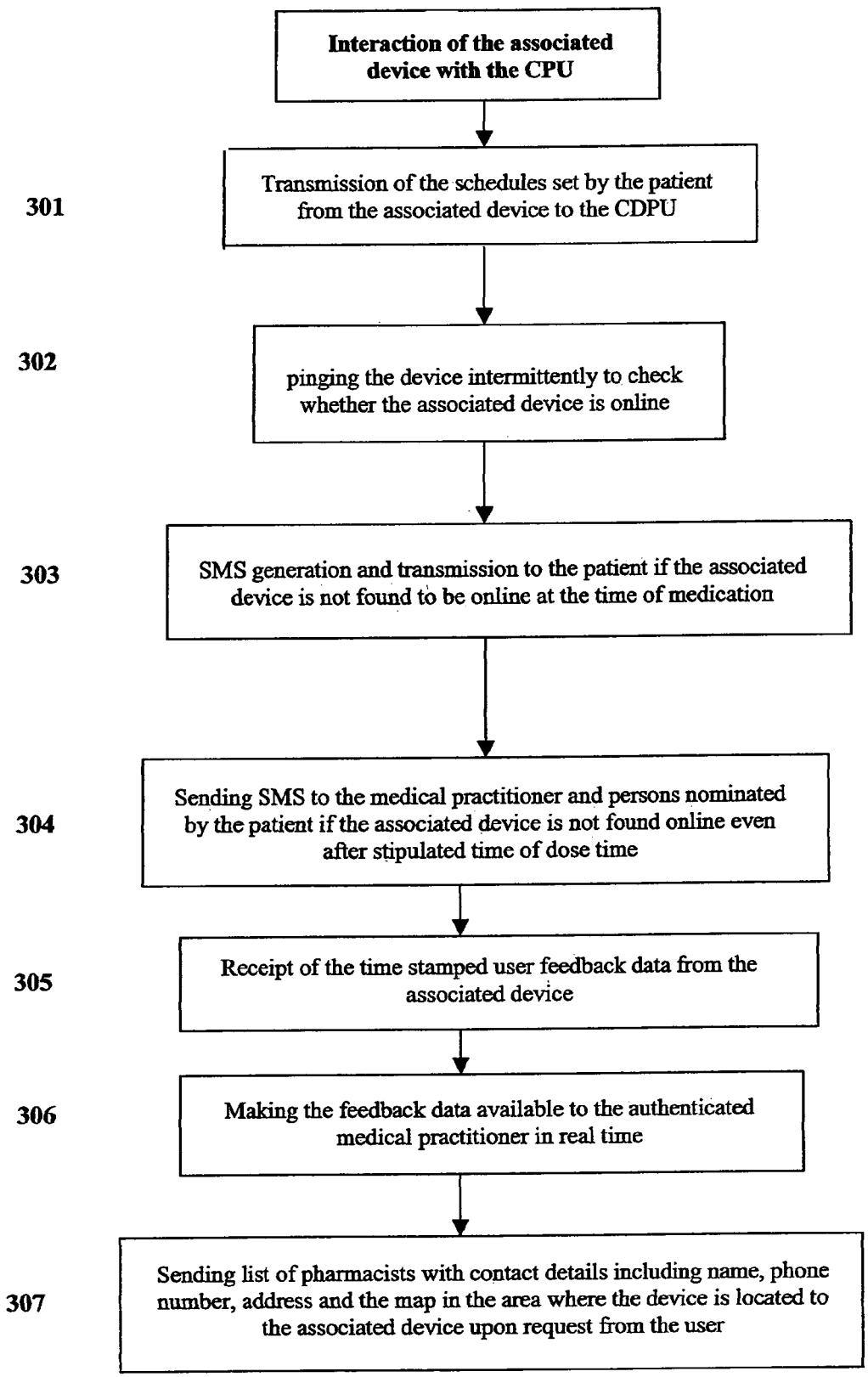

FIG. 2*b* Steps of interaction of the patient medication system including associated device with the remote system (Sheet 4)

Figure 2C:
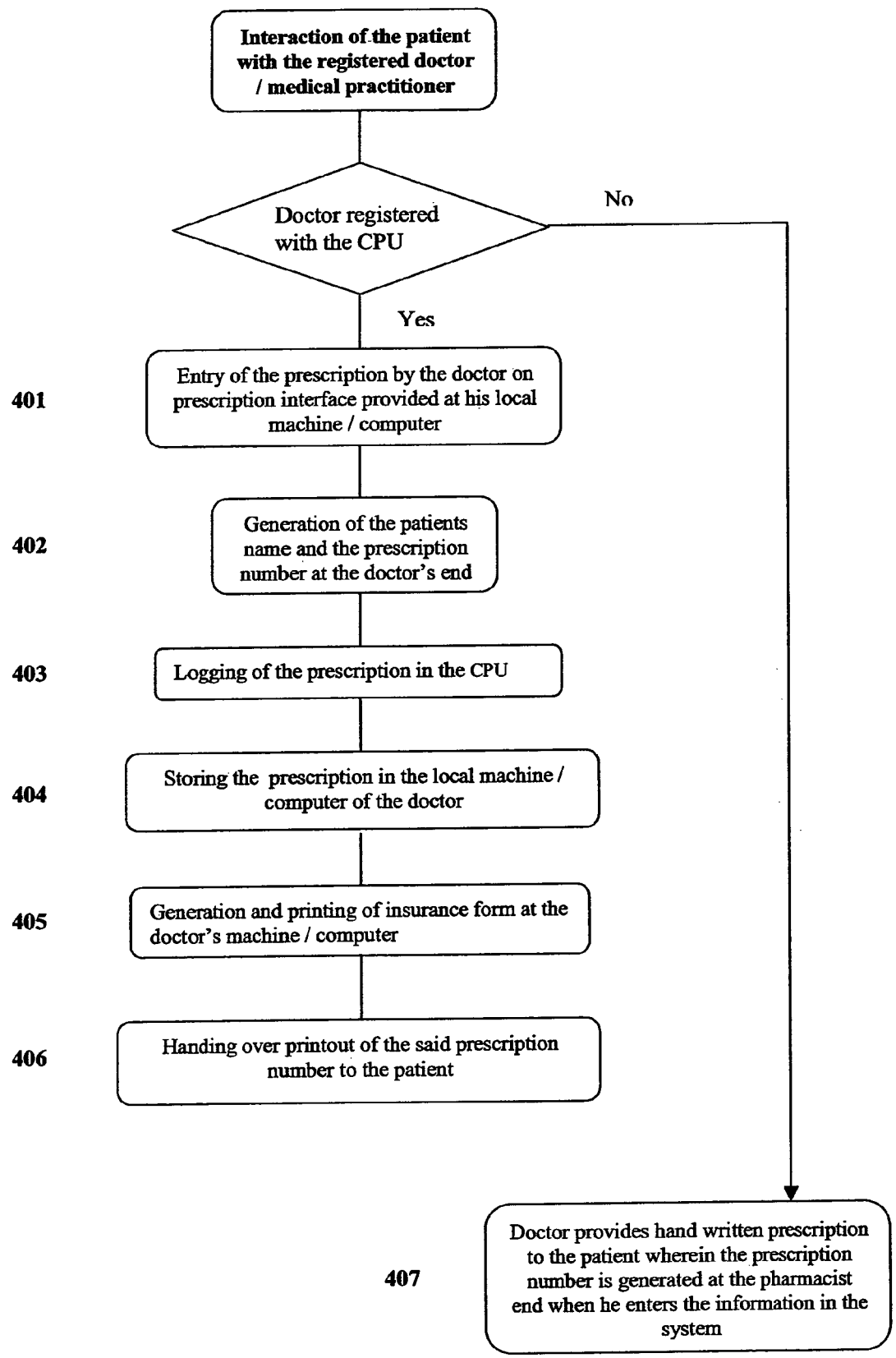

FIG. 2*c* Steps of Interaction of the patient with the registered doctor/medical practitioner (Sheet 5)

Figure 2D:
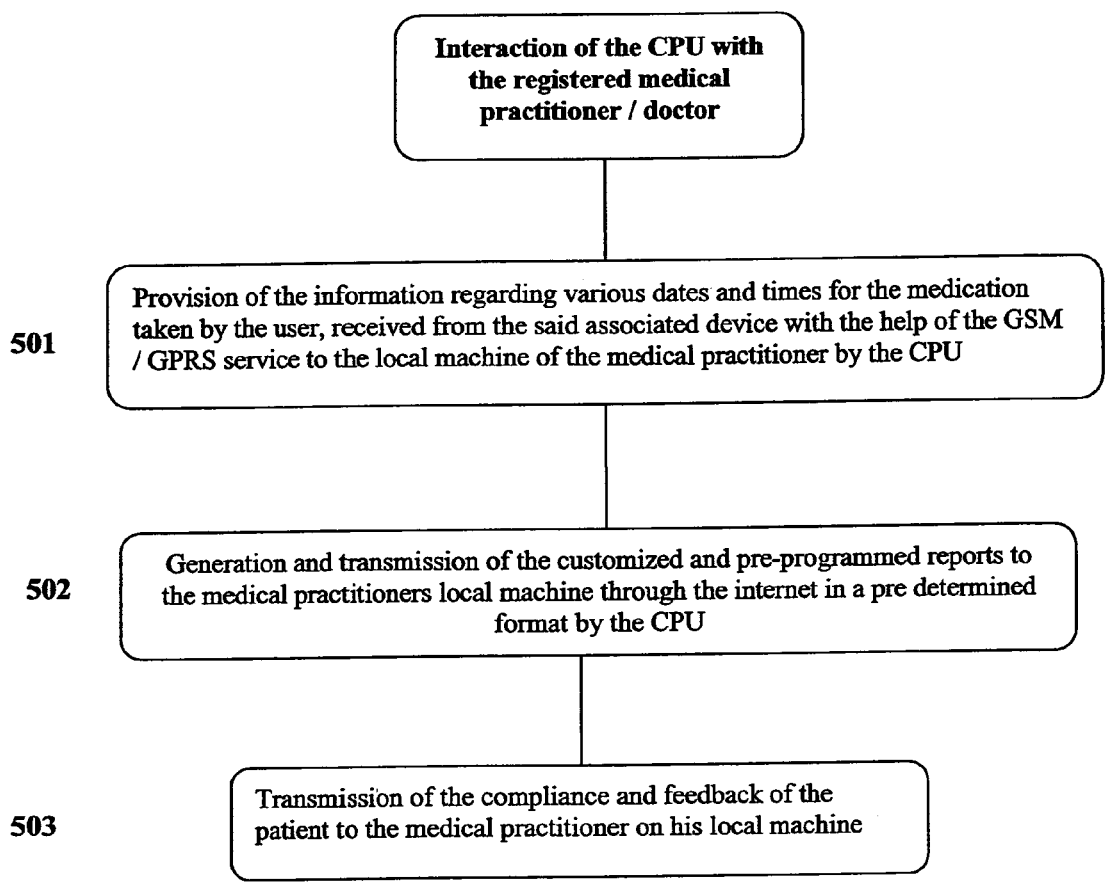

FIG. 2*d* Steps of Interaction of the remote system with the registered medical practitioner/doctor (Sheet 6)

Figure 2E:
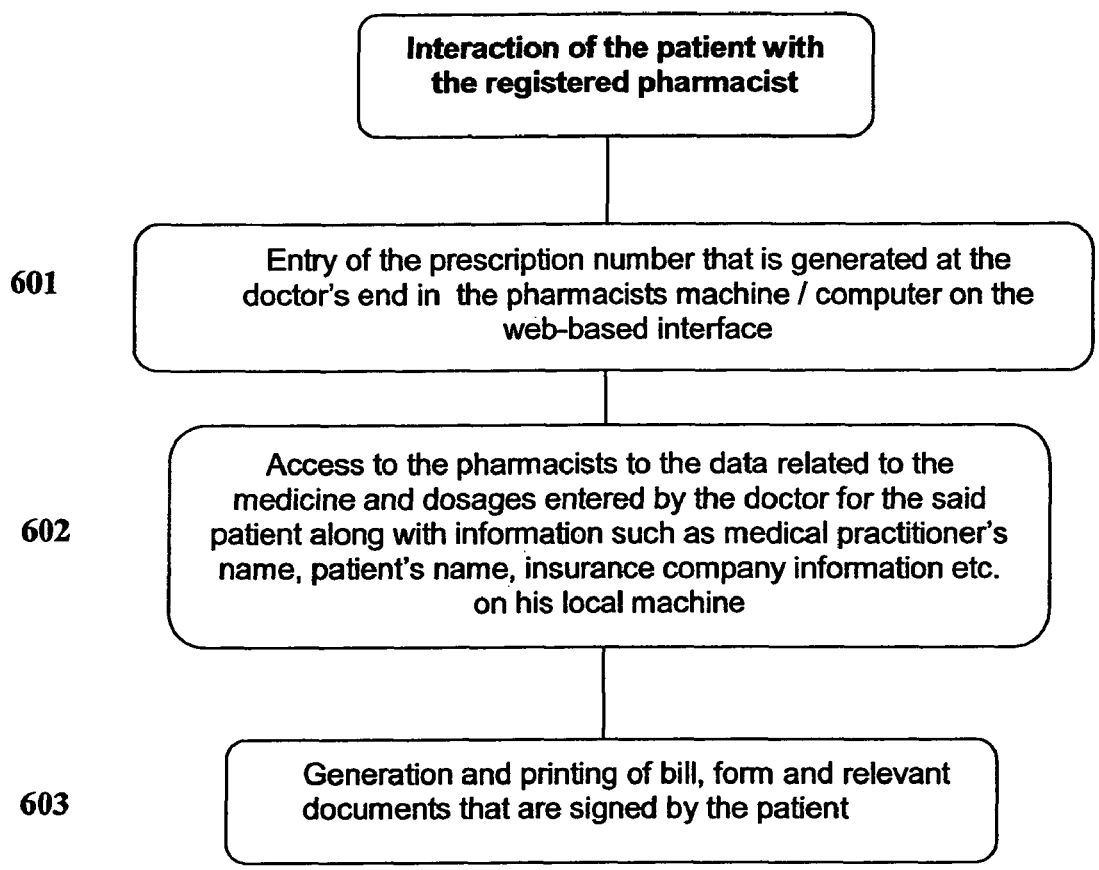

FIG. 2*e* Steps of interaction of the patient with the registered pharmacist (Sheet 7)

Figure 2F:
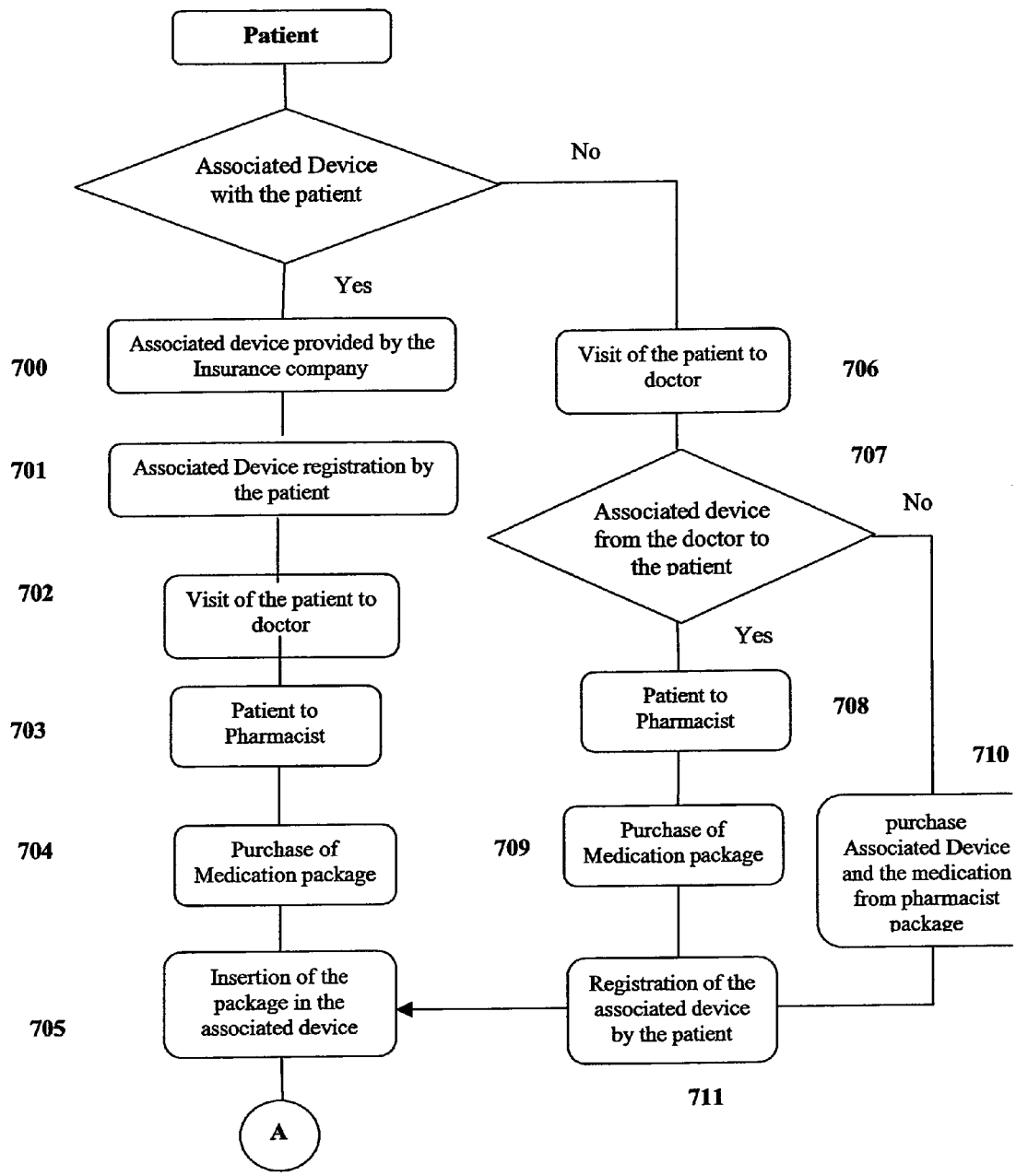

FIG. 2*f* Source of the associated device to the patient (Sheet 8)

FIG. 1*a* illustrates conventional healthcare system wherein patient 5 interacts with various healthcare agencies such as medical practitioner 6, pharmacists 7, distributor 8, pharmaceutical company 9 and health insurance agency 10. The said healthcare agencies are isolated and there is one way interaction with the patient. The patient is not liked with all the healthcare agencies and the healthcare agencies are also not liked with each other in the conventional system/process.

FIG. 1*b* illustrates comprehensive integrated healthcare system of the present invention to integrate patient 5 with healthcare agencies such as medical practitioner 6, pharmacists 7, distributor 8, pharmaceutical company 9 and health insurance agency 10, clinical researcher (not shown) but not limited to it. The patient 5 along with the medication system 2 is integrated with various healthcare agencies via remote system 4 and communication ports 6*p*-10*p* wherein the patient medication system in one of the embodiments comprises medication in a package and an associated device 1, the package being adapted to communicate with the associated device and the associated device being communicably linkable to the remote system.

The said comprehensive integrated healthcare system relating to a patient is interactive between a first healthcare agency and at least one other party, the said other party being selected from the patient and at least one other healthcare agency. The system comprises of a remote system 4 for storing a defined healthcare regime for the patient and optionally other data relating directly or indirectly to the healthcare regime; a patient medication system 2 for use by the patient providing medication to be taken by the patient; a communication port 3 for at least one healthcare agency to communicate interactively with the remote system 4;

wherein;

the remote system 4 and the patient medication system 2 are linked and interactively communicable whereby information relating to the healthcare regime is transmissible to the patient medication system 2 and accessible by the patient 5 and information relating to the patient medication system 2 is transmissible to the remote system 3 and comparable with the defined healthcare regime stored in the system; and the communication port 3 is adapted for the at least one healthcare agency to input information and/or to receive information relating to the healthcare regime of the patent by transmission of information between the communication port 3 and to the remote system 4; the arrangement being such that the first healthcare agency and at least one other party, the said other party being selected from the patent and at least one other healthcare agency transmit and/or receive via the remote system 4 information relating directly or indirectly to the healthcare regime of the patient The system operates in steps of:

i. registering a defined healthcare regime for the patent in a remote system and optionally other data relating directly or indirectly to the healthcare regime;

j. providing to the patient a patient medication system comprising a package comprising a product for dispensing, information relating to the identity of the package and the patient medication system being communicably linked to the remote system;

k. recording information relating to the identity of the package in the patient medication system or remote system and whereby upon dispensing of the product the said recorded information is comparable with the information of the package to determine whether or not the information of the said product dispensing system corresponds with the said recorded information;

l. providing to the at least one healthcare agency a communication port communicably linked to the remote system;

m. periodically providing information relating to the identity of the patient and/or the status of the package from the patient medication system to the remote system;

n. comparing the information periodically transmitted to the remote system with the healthcare regime recorded for the patient in the remote system to ascertain whether the information corresponds with the recorded healthcare regime;

o. optionally providing information from the remote system to the patient medication system to indicate whether the status of the patent medication system and/or identity of the patient corresponds with the information relating to the healthcare regime and/or the identity of patent;

p. providing information from the remote system to the at least one healthcare agency indicating that a periodic transmission of information has been received by the remote system;

whereby the first healthcare agency and at least one other party, the said other party being selected from the patent and at least one other healthcare agency transmit and/or receive via the remote system information relating directly or indirectly to the healthcare regime of the patient. Further, the said health care agencies may also be in liaison with each other through the said remote system 4.

The said system results in the useful, tangible and concrete technical effect of authentication of the medication package 2 against counterfeit, authentication of the said health care agencies; compliance of medication intake at prescribed times by the medical practitioner; maintaining health diary that includes health indicators such as maintenance of health records/feedback of a user including indications like blood pressure, heart rate, blood sugar level, headache, nausea, diziness etc.; data and Information including those obtained in clinical research and pharmacovigilance wherein secured database is maintained at various terminals including said associated device 1, local machine of the medical practitioner, the said web portals and the said remote system 4; liaising with the said healthcare agencies including medical practitioners, users, persons nominated by the user, clinical researchers, pharmacists, pharmaceutical companies, insurance agencies etc.

FIG. 2 and subsequent figures from FIG. 2a to FIG. 2f depict the steps of the system operation. FIG. 2 indicates the interactions of the patient with various healthcare agencies such as doctor, pharmacist, insurance agency, clinical researchers, distributor etc. in the healthcare chain. The subroutines indicated as A, B, C etc. corresponding to each of the step are separately elaborated in sub FIGS. 2a to 2f. It is implied that all the said healthcare agencies are registered with the remote system 4 of the system illustrated in FIG. 1. As shown in the FIG. 2 the associated device of the patient medication system 1 is registered with the said remote system 4. In the further step, the registration is confirmed from the remote system 4. Further, the system operates in various steps as shown in the figure from steps 101 to 107 in terms of interactions of the patient with the said healthcare agencies via said remote system 4 and corresponding said web portals 6p-10p.

FIG. 2a depicts steps of interaction of the patient with the associated device of the medication system. The patient can access the associated device 1 only if his/her registration is carried out with the medication system. The method comprises of:

i) providing a unique identifier for the associated device 1 of the patent and recording the identifier with the healthcare regime of the patient in the remote system 4 to register the associated device 1;

ii) optionally receiving a confirmation signal of the registration from the remote system 4;

iii) registering the patent with the associated device 1 in the remote system 4;

iv) registering the healthcare regime of the patient in the remote system 4;

v) engaging the package of the patient medication system into the associated device 1;

vi) comparing the recorded information which relates to the identity of the package and which is stored in the associated device 1 or remote system 4 with the information of the package engaged with the associated device 1 to determine whether or not the information of the engaged package corresponds with the said recorded information; and;

vii) provided the information of the package corresponds to the stored information relating to the identity of the package, registering the package with the associated device in the remote system;

whereby information is provided to the remote system 4 linking the package and associated device 1 with the healthcare regime of the patient so as to enable authentication and registration of the medication package identity.

After registration of the patient with the said associated device, as indicated by step 201 in the figure, the patient inputs medication schedule and sets alarm times in predetermined range with reference to the prescription in the associated device 1. Further, patient inserts medication package 2 into the said associated device 1 as indicated in step 202. In the further step, 204, registration of the said package 2 with the said associated device 1 is carried out and further authentication of the said package 2 is checked in the associated device 1. The process continues only if the package authentication is confirmed by the said associated device. In the next step 205, the compliance with the medication schedule is monitored by sensing presence/absence of the medication in the said package by the said associated device. Further, the device also provides reminders at the medication timing to the patient The process concludes with the step 206 wherein post medication feed back by is entered in the said associated device by the patient.

The medication system interacts with the remote system 4 to detect compliance of the patient with the healthcare regime. The healthcare regime is stored in the remote device 4 by inputting the healthcare regime/schedule or clinical trial protocol in the associated device 1 of the patient medication system and communicating the healthcare regime from the patient medication system to the remote system 4 and storing the regime in the remote system 4 as indicated in FIG. 2b in step 301. The method for detecting compliance of the patient with the healthcare regime comprises of i. storing the healthcare regime of the patient in the remote device;

ii. periodically checking that the patient medication system is communicably linked to the remote system 4;

iii. where the patient medication system has not been communicably linked to the remote system after a predetermined time to validate adherence to the healthcare regime, generating and transmitting a message to the patient to link the patent medication system to the remote system 4;

iv. where the patient medication system is not communicably linked to the remote system 4 after a pre-set delay from the time of transmission of the message in step iii), generating and transmitting a message to at least one of the medical practitioner of the patient or a nominated individual indicating noncompliance of the patent with the healthcare regime; and v. where the patient medication system is communicably linked to the remote system, recording information in the remote system relating to the time of the link and the identity and status of the package and providing access to the said information to the medical practitioner.

The particulars are indicated in FIG. 2b. The system operates in steps of transmission of the regime/schedules set by the patient mentioned in the previous step from the associated device 1 of the medication system to the remote system 4 as shown in step 301; pinging the device intermittently to check whether the associated device 1 is online in step 302; SMS generation and transmission to the patient if the associated device 1 is not found to be online at the time of medication in step 303; sending SMS to the medical practitioner/doctor and persons nominated by the patient if the associated device 1 is not found online even after stipulated time of dose time in step 304; receipt of the time stamped user feedback data from the associated device 1; making the feedback data available to the authenticated medical practitioner in real time as shown in step 305; making the feedback data available to the authenticated medical practitioner in real time as shown in step 306; sending list of pharmacists with contact details including name, phone number, address and the map in the area where the device is located to the associated device upon request from the user as shown in step 307.

FIG. 2c illustrates process steps in the Interaction of the patent with the registered doctor/medical practitioner. If tie doctor is registered with the remote system 4, he enters prescription on prescription interface provided at his local machine/computer as indicated in step 401. Further, Generation of the patients name and the prescription identifier number takes place at the medical practitioner/doctor's end as indicated in step 402. The said prescription is logged in the said remote system 4 in step 403. The prescription is also saved in the local machine of the doctor as shown in step 404. As shown in step 405, insurance form is generation and printed at the doctor's machine/computer. The printout is handed over to the patient (step 406). If the doctor is not registered with the remote system 4, he/she provides hand written prescription to the patient wherein the prescription number is generated at the pharmacist end when he enters the information in his local machine/computer (step 407). The method of generation of the prescription identifier for a patient to whom a medical prescription has been issued by a health care agency, preferably a medical practitioner, comprising:
 i) either:
  a) generation by a pharmacist of a prescription identifier on presentation of the prescription the identifier comprising the healthcare regime and information relating to the patient; or
  b) generation by the medical practitioner of a prescription identifier comprising the healthcare regime and information relating to the patient;
 ii) communicating the prescription identifier to the remote system via a communication port to which the pharmacist or medical practitioner has access.

FIG. 2d indicates interaction of the remote system 4 with the registered medical practitioner/doctor/clinical researcher. The steps comprises of the following:
 provision of the information regarding various dates and times for the medication taken by the patient, received from the said associated device 1 with the help of the GEM/GPRS service to the local machine of the medical practitioner/doctor by the said remote system 4 (step 501); generation and transmission of the customized and pre-programmed reports to the medical practitioners/doctor local machine through the internet in a pre determined format by the remote system 4 as shown in step 502 and transmission of the compliance and feedback of the patient to the medical practitioner/doctor/clinical researcher on his local machine as shown in step 503.

FIG. 2e illustrates steps in the interaction of the patient with the registered pharmacist. The prescription identifier is retrieved by the pharmacist from the remote system optionally he can enter the prescription identifier (that is generated at the medical practitioner's end) in the pharmacists machine/computer on the web-based interface as shown in step 601; access to the pharmacists to the data related to the medicine and dosages entered by the doctor for the said patient along with information such as medical practitioner's name, patient's name, insurance company information etc. on his local machine (step 602); generation and printing of bill, form and relevant documents that are signed by the patient (step 603).

FIG. 2f depicts the source of the associated device 1 to the patent. The associated device 1 may be subscribed to the patient by the insurance agency. In this case, patient registers the associated device 1 with the remote system 4 (step 701); the patent visits pharmacists, purchases the medication package (step 702-705) and the process continues as illustrated in FIG. 2a. The case wherein the associated device 1 is not subscribed by the insurance agency, the patient visits doctor, collects prescription and purchases the said associated device 1 from the pharmacists end (step 710) followed by registration of the patent with the said associated device 1 (step 709); the patent can also purchase the associated device from doctor (step 706, 707); patient registers with the associated device 1 (step 711); the patient inserts the medication package in the said associated device 1 and the process continues as illustrated in FIG. 2a.

In one of the embodiments the patient medication system comprises: a package containing medication and which has information relating to the identity of the package; and an associated device 1 with which the package is engagable, the associated device 1 being communicably linked to the remote system 4 and registrable with the remote system 4;and recording information relating to the identity of the package in the associated device 1 or remote system 4 whereby upon engagement of the package and associated device 1 the said recorded information is comparable with the information of the package to determine whether or not the information of the engaged package corresponds with the said recorded information; and optionally providing information from the remote system 4 to the associated device 1 to indicate whether the status of the package and/or identity of the patient corresponds with the information relating to the healthcare regime and/or the identity of patent The associated device comprises of:
 interactive and/or user input means; powered time tracking means; data decoding means, data processing, data storage means; analog to digital converter, data sampling and organizing means so configured to communicate with an external data source so as to one or more of register the product user, authenticate, register product package when housed/located in the said housing and optionally carry out transient data collection or communicate with and/or through a remote or integrated data system optionally for the collection, transmission, collation, archival or dissipation of transient data or information provided by the user or combinations thereof.

In yet another embodiment the patient medication system comprises of an interactive smart package—associated device comprising a smart package for carrying a product and which is adapted to communicate with an associated device, the package comprising a plurality of containments adapted to receive a product, each containment being closed or optionally with closure means, the said plurality of containment/s and/or closure/s being non-electrically interconnected; signal generating means adapted to convey to an associated device information relating to one or more of the containments; a chip, the said chip being optional when signal generating means itself is a chip and optionally transmitter and/or receiver means; the said associated device comprising a housing adapted to communicate with the smart package; signal sensing for detecting a signal from the signal generating means said signal sensing optionally comprising acquiring means configured with data input, storing, output, decoding and processing and communicating means adapted to communicate with an external data record;

wherein said signal generating means is disposed in the said package such that, on communication with the device, the signal generating means provides information relating to one or more of the containments to the signal sensing means in the said associated device and optionally the information is communicated externally of the said system for the purpose of comparison of the information with the external data record.

In one of the variants of this interactive-smart package medication system embodiment the associated device comprises a housing with package holding provision adapted to receive the package containing a product; a signal generator adapted to determine information relating to the presence or absence of the product in the package and signal sensing means provided in the said device to detect signals generated by the said signal generator providing information relating to the product; a patient interface whereby the patient may input information or receive information relating to the healthcare regime from the remote system the arrangement being such that the device is registrable to the patient; the package is registrable to the device; and the identity and/or status of the package and device are comparable to the healthcare regime for the patient so as to enable authentication of the identify and/or status of the package to determine compliance or otherwise of the patient with the healthcare regime.

In one of the variants of this embodiment the smart package comprises a plurality of containment/s adapted to receive a product, each containment being closed or optionally with closure means wherein the containment/s and/or closure/s are non-electrically-interconnected; chip and optionally transmitter and/or receiver means; signal generating means provided in or optionally on the containment/s, or in or optionally on the said closure/s such that removal of product/s from the said containment/s generate signal and/or alter the signal detected by the signal sensing means in the said associated device.

In yet another variant the smart package comprises containment/s in the form of one or plurality of enclosed spaces formed in a first lamina to contain the product closed with second rupturable lamina attached to the first lamina to form a closure so as to seal the product in the said enclosed spaces; the said containment/s and/or closure/s being non-electrically interconnected; chip and optionally transmitter and/or receiver means.

In yet another variant one or a plurality of magnets are disposed on or in the smart package and adapted to provide information relating to the location, portion or zone of one or more of the products in the said enclosed space/s of the containment/s.

In another variant the said containment or closure means is provided with magnetic ink which encodes information relating to the location, portion or zone of one or more of the products in the said enclosed spacers of the containment/s optionally by having specific strength on areas corresponding to the location, portion or zone of the product in the said enclosed spacers of the containment/s.

In another variant the smart package comprises a carded/walletized package system which comprises:

carding comprising a first lamina provided with openings corresponding to the said formed enclosed spaces of the said package such that the said formed enclosed spaces pass through the said openings; a second lamina provided with perforated peelable portions provided corresponding to or aligned with the locations of the said rupturable lamina of the package such that when the product in the package is removed, the said perforated portion corresponding to that product is also removed; the package comprising a plurality of containments in the form of a first package lamina in which one or a plurality of enclosed spaces are formed to contain the product(s) closed with a second package rupturable lamina attached to the unformed portion of the first package lamina to seal the product(s) in the said enclosed spaces; the said containment/s and/or closure/s being non-electrically interconnected; chip and optionally transmitter and/or receiver means;

wherein the said package is placed between the first and the second lamina of the said carding; signal generating means in or optionally on the containment/s, or in or optionally on the said closure/s.

In yet another variant the smart package comprises of product containment in the form of a flexible material wherein part of the same material is sealed to form a pouch and a closure means in the form of a product entrapment and dispensing provision; signal generating means provided in the said product entrapment and dispensing provision means such that removal of the product from the said containment portion results in generation of signal and/or alteration of the signal; chip and optionally transmitter and/or receiver means.

In one of the variants the signal generating means of the smart package generates a signal in the form of magnetic field or modifies a magnetic field. In yet another variant, the signal generated from the signal generating means is generated from the smart package resulting from a change in the physical, electrical, thermal, optical, visual property, characteristics or signal of the smart package.

In yet another variant the package comprises of a multipolar or unipolar sheet capable of being pre-magnetized and which is disposed so as to be disturbed by the removal of a product from a containment in the smart package.

In another variant, the smart package is provided with a customized pattern representing information relating to the location, portion or zone of product in the containment/s to generate a signal and/or after a signal generated and/or detected by the signal sensing means in the said associated device caused by removal of product/s from the said containment/s.

In one of the embodiments of the package of the medication system the smart package comprises a first sheet having multiple containment capsules upstanding from a first surface thereof and dimensioned to receive individual product items and multiple corresponding openings in a second surface of the sheet to the upstanding capsules; a second sheet secured to the second surface of the first sheet so as to provide closures over the multiple openings in the first sheet; and components having individual signatures and being disposed adjacent corresponding closures such that respective signatures are substantially detectable only if their corresponding closures are intact. In one of the variants of this embodiment the respective components include respective discrete magnets respectively secured to the second sheet opposite openings to corresponding upstanding containment capsules; and wherein the substantially detectable signatures comprise respective magnetic fields. In another variant of this embodiment the respective components include respective magnetic layers disposed upon the second sheet opposite openings to corresponding upstanding containment capsules; and wherein the substantially detectable signatures comprise respective magnetic fields. In another variant of this embodiment the respective components include respective light reflecting surface regions integral with the second sheet opposite openings to corresponding upstanding containment capsules; and wherein the substantially detectable signatures comprise reflection of light. In another variant of this embodiment the respective components include respective light absorptive surface regions integral with the second sheet opposite openings to corresponding upstanding containment capsules; and wherein the substantially detectable signatures comprise absorption of light. In yet another variant the respective components include respective electrical components disposed upon the second sheet opposite openings to corresponding, upstanding containment capsules; and wherein the substantially detectable signatures comprise an electrical characteristic of the respective electrical components.

In another embodiment the smart package of the medication system comprises:

a product package that includes; an entrapment region to contain a product; a removable closure that encloses the product within the entrapment region prior to its removal and that allows passage of the product from the entrapment region upon its removal;

a component having signatures and being disposed adjacent the closure such that the signatures is substantially detectable only if the closures is intact; a reader that includes, a sensor to sense signature when a product is disposed within the entrapment region; and a receptor region contoured to receive at least a portion of the product package that includes the entrapment region and to align the sensor with the entrapment region to permit sensing of the signature prior to removal of the closure while the product is disposed within the entrapment region. One of the variants of this embodiment comprises of first data storage circuitry secured to the package and encoded with first information; second data storage circuitry secured to the reader and encoded with second information; processing circuitry associated with the reader to process the first information and the second information to authenticate the package; and a communication interface to communicate information between the first data storage circuitry and the second data storage circuitry and the processing circuitry.

In yet another variant the processing circuitry is coupled to receive a sensor signal indicative of receipt of a signal imparted by the signal generator; and a communication interface to communicate information externally to the reader that is indicative of the imparting of a signal generated by the signal generator through a free space in the entrapment region to the sensor in the absence of the product within the entrapment region. In another variant the processing circuitry is coupled to receive a sensor signal indicative of detection of the signature; and a communication interface to communicate information externally to the reader that is indicative of whether the signature has been detected.

In another embodiment the smart package of the medication system includes an entrapment region to contain a product; a reader that includes, a signal generator to impart a signal across a free space; a sensor to sense the signal generated by the signal generator across the free space; a receptor region sized to receive at least a portion of the product package that includes the entrapment region and contoured to align the signal generator and the sensor with the entrapment region to permit the signal generator to impart a signal through a free space in the entrapment region to the sensor in the absence of the product within the entrapment region.

In one of the variants, the smart package further comprises first data storage circuitry secured to the package and encoded with first information; second data storage circuitry secured to the reader and encoded with second information; processing circuitry associated with the reader to process the first information and the second information to authenticate the package; a first communication interface to communicate information between the first data storage circuitry and the second data storage circuitry and the processing circuitry; processing circuitry coupled to receive a sensor signal indicative of receipt of a signal imparted by the signal generator; and a second communication interface to communicate information externally to the reader that is indicative of the imparting of a signal generated by the signal generator through a free space in the entrapment region to the sensor in the absence of the product within the entrapment region.

In another embodiment the smart package includes;

an entrapment region to contain a product; a removable closure that encloses the product within the entrapment region prior to its removal and that allows passage of the product from the entrapment region upon its removal; a magnetic material associated with the closure; a reader that includes, a sensor to sense a magnetic signal imparted by the magnetic material when the product is disposed within the entrapment region; and a receptor region contoured to receive at least a portion of the product package that includes the entrapment region and to align the sensor with the entrapment region to permit the magnetic material to impart a magnetic signal to the sensor prior to removal of the closure while the product is disposed within the entrapment region; first data storage circuitry secured to the package and encoded with first information; second data storage circuitry secured to the reader and encoded with second information; processing circuitry associated with the reader to process the first information and the second information to authenticate the package; a first communication interface to communicate information between the first data storage circuitry and the second data storage circuitry and the processing circuitry; processing circuitry coupled to receive a sensor signal indicative of receipt of a signal imparted by the magnetic material; and a second communication interface to communicate information externally to the reader that is indicative of the imparting of a signal by the magnetic material to the sensor in the absence of the product within the entrapment region.

In another embodiment the patient medication system comprises a package system comprising:

an embedded system comprising data logging and storing means comprising optionally a data processing means, communication/interaction means;

a power source built-in or optionally induced;

non-accessible compartment for the said embedded system;

a separate non-accessible product containment;

a means for authentication such as an encoded chip or a pattern or a random pattern or a marker or combinations thereof;

optional display/interactive means;

a sensing means that activates/deactivates upon dispensing of the product from the package;

means to establish connection of the power source with the said operating system;

wherein the said embedded system is configured with the sensing means and optionally with authentication means and is housed in the said compartment wherein the said compartment is operably connected with the said containment;

wherein
the said package is authenticated by the remote system;
optionally prompting product consumption;
the said sensing means senses the product dispense, the said operating system records and transmits/communicates real time product dispense data via said interaction/communication means to the remote device,
rendering the package un-authentic in case of compromise/tampering.

In a specific embodiment of this invention when used in clinical trials, it provides a method for interactively collecting pharmacovigilance data relating to a patient by:
i. providing to the patient means to provide feedback of information from the patient to the remote system said information relating to the condition of the patient and/or response to medication taken during the clinical trails;
ii. periodically providing information relating to the condition of the patient and/or response to medication taken during the clinical trial to the remote system.

Further it provides a method wherein the system may comprises a device to monitor or measure one or aspects of the medical condition of the patient such as his temperature, blood pressure, etc, and the information is periodically communicated to the remote system either automatically or manually.

Thus in clinical trials this integrated healthcare management system provides an interactive means between at least one patient in the clinical trial and a party carrying out a clinical trial for collection of collection of pharmacovigilance data wherein the system comprises:
i) registering a defined healthcare regime (i.e. protocol) for the patient in a remote system and optionally other data relating directly or indirectly to the healthcare regime (protocol);
ii) providing to the patient a patient medication system comprising a package comprising a product for dispensing, information relating to the identity of the package and the patent medication system being communicably linked to the remote system;
iii) optionally recording information relating to the identity of the package in the patient medication system or remote system and whereby upon dispensing of the product the said recorded information is comparable with the information of the package to determine whether or not the information of the said product dispensing system corresponds with the said recorded information;
iv) providing to the party carrying out the clinical trial a communication port communicably linked to the remote system;
v) periodically providing information relating to the identity of the patient and/or the status of the package from the patient medication system to the remote system;
vi) comparing the information periodically transmitted to the remote system with the healthcare regime recorded for the patient in the remote system to ascertain whether the information corresponds with the recorded healthcare regime;
vii) optionally providing information from the remote system to the patient medication system to indicate whether the status of the patient medication system and/or identity of the patient corresponds with the information relating to the healthcare regime and/or the identity of patient;
viii) optionally providing information from the remote system to the party carrying out the clinical trial indicating that a periodic transmission of information has been received by the remote system;
whereby the party carrying out the clinical trial may determine whether the patient has complied with the healthcare regime.

Thus it is evident that the present invention provides a method and an integrated healthcare anti-counterfeit management system relating to a patient which is interactive between a first healthcare agency and at least one other party, the said other party being selected from the patient and at least one other healthcare agency wherein patient is at the focal point (patient centric method) and healthcare agencies such as medical practitioners, health insurance agency, healthcare regulators, pharmaceutical companies, clinical researcher, pharmacies and medication package are integrated with the patient and also are in liaison with each other via authenticated and registered process to provide the useful technical effect of:
authentication of the medication package against counterfeit wherein the system identifies and confirms the source of the medication package and accesses information such as manufacturing date, expiry date, place of manufacture, geographical validation in that area etc.;
registration and authentication of the associated device and various stakeholders including medical practitioners, pharmacists and users to the remote system;
user compliance to doctors prescription wherein SMS is generated and sent to the patient if the associated device is not found to be online at the time of medication; SMS is sent to the medical practitioner and people nominated by the patient at the time of registration if the associated device is found not to be online even after substantial time lapse after dose time;
recording user compliance to medication and acquiring patient feedback on the effects of the medication including during clinical trials/research and pharmacovigilance
patient feedback wherein user enters post medication feedback in the medication system that is time stamped and transferred to the server wherein the said data is available for a authenticated practitioner in real time;
generation of the prescription at the doctors end and further storage of the same at the remote system level and doctors end;
generation and transmission of customized and preprogrammed reports for the medical practitioners at his/her local machine through the internet in a pre determined format;
maintaining secured data and information for various stake holders at including said associated device;
providing real-time and authentic data in raw and analysed form to diverse agencies in the healthcare chain; creating statistical and other reports that can be accessed by healthcare agencies groups by means including websites/ftp sites;
creating documentation of the dosage uptake by the users;
facility at the pharmacists end to see the medicine and dosages entered by the medical practitioner/doctor for the patient along with information such as medical practitioner's name, patient's name, insurance company information etc.;
reminder/alert provision to distributor on his local machine/computer through desktop cookie information about "low stock" at particular pharmacy for particular brand;

access to the distributor to the database on the said remote system about the sell pattern of particular brand of medicine and volumes of the same;

provision for pharma company to track stocks available with all distributors and replenish stock through the database;

liaisoning with the said healthcare agencies including medical practitioners, users, persons nominated by the user, pharmacists, clinical researchers, pharmaceutical companies, insurance agencies etc.;

registered pharma company can track stocks available with all distributors and replenish stock through the database;

interaction of insurance agency directly with the patient and through the remote system as well;

to the patient.

We claim:

1. A method of providing an integrated healthcare management system relating to a patient which is interactive between a first healthcare agency and at least one other party, said other party being selected from the patient and at least one other healthcare agency, the method comprising:
   i. registering a defined healthcare regime for the patient in a remote system;
   ii. providing to the patient a patient medication system comprising:
      a. a package comprising a product for dispensing and information relating to the identity of the package;
      b. an associated device with which the package is engagable so as to be readable by the associated device, the associated device being communicably linked to the remote system and registrable with the remote system;
   iii. the patient medication system being communicably linked to the remote system through the associated device;
   iv. recording information relating to the identity of the package in the associated device or remote system whereby upon engagement of the package and the associated device, the recorded information is comparable with the information of the package to determine whether or not the information of the engaged package corresponds with the recorded information;
   v. recording information relating to the identity of the package in the patient medication system or remote system and whereby upon dispensing of the product said recorded information is comparable with the information of the package to determine whether or not the information of said package corresponds with said recorded information;
   vi. providing a unique identifier for the associated device and recording the identifier with the healthcare regime of the patient in the remote system to register the associated device;
   vii. registering the patient with the associated device in the remote system;
   viii. engaging the package of the patient medication system into the associated device;
   ix. comparing the recorded information which relates to the identity of the package and which is stored in the associated device or remote system with the information of the package engaged with the associated device to determine whether or not the information of the engaged package corresponds with said recorded information;
   x. provided the information of the package corresponds to the stored information relating to the identity of the package, registering the package with the associated device in the remote system;
      whereby information is provided to the remote system linking the package and associated device with the healthcare regime of the patient so as to enable authentication and registration of the medication package identity;
   xi. providing to the at least one healthcare agency a communication port communicably linked to the remote system;
   xii. periodically providing information relating to the identity of the patient and/or the status of the package from the patient medication system to the remote system;
   xiii. comparing the information periodically transmitted to the remote system with the healthcare regime recorded for the patient in the remote system to ascertain whether the information corresponds with the recorded healthcare regime;
   xiv. providing information from the remote system to the at least one healthcare agency indicating that a periodic transmission of information has been received by the remote system;
      whereby the first healthcare agency and at least one other party are able to transmit and/or receive via the remote system information relating directly or indirectly to the healthcare regime of the patient.

2. A method according to claim 1 wherein the patient medication system comprises a package system comprising:
   a dispensing system with an optional product outlet provision;
   an embedded system comprising a data logging and storing device;
   a power source;
   a non-accessible compartment for said operating system;
   a separate non-accessible product containment;
   an authentication element
   a sensing means that activates or deactivates upon dispensing of the product from the package;
   the power source being connected with said operating system;
   wherein said operating system is configured with the sensing means and is housed in-the said non-accessible compartment wherein said non-accessible compartment is operably connected with said separate non-accessible containment;
   wherein said package is authenticated by the remote system; and
   said sensing means senses the product dispensed, said operating system records and transmits or communicates real time product dispense data to the remote device, rendering the package un-authentic in case of compromise or tampering.

3. The method of claim 2 further wherein the data logging and storing device comprises a data processor.

4. The method of claim 2 wherein the authentication element comprises an encoded chip, a pattern, a random pattern, a marker or combinations thereof.

5. The method of claim 2 wherein said operating system is configured with the authentication element.

6. A method according to claim 1 further including detecting compliance of the patient with the healthcare regime, the healthcare regime requiring administration of medication at a predetermined time, the method comprising:
   i) periodically checking that the patient medication system is communicably linked to the remote system;
   ii) where the patient medication system has not been communicably linked to the remote system after a predetermined time to validate adherence to the healthcare regime, generating and transmitting a message to the patient to link the patient medication system to the remote system;

iii) where the patient medication system is not communicably linked to the remote system after a pre-set delay from the time of transmission of the message in step ii), generating and transmitting a message to at least one of the medical practitioner of the patient or a nominated individual indicating non-compliance of the patient with the healthcare regime; and iv) where the patient medication system is communicably linked to the remote system, recording information in the remote system relating to the time of the link and the identity and status of the package and providing access to said information to the medical practitioner;

wherein the healthcare regime is stored in the remote device by inputting the healthcare regime in the patient medication system and communicating the healthcare regime from the patient medication system to the remote system and storing the regime in the remote system.

7. A method according to claim 1 for further including generating a prescription identifier for a patient to whom a medical prescription has been issued by a health care agency, comprising:

i) generation of a prescription identifier, on presentation of the prescription the identifier comprising the healthcare regime and information relating to the patient ii) communicating the prescription identifier to the remote system via a communication port;

wherein the prescription identifier is retrievable by a pharmacist from the remote system upon presentation of the prescription identifier and may be used to make up the medication of the package of the patient.

8. A method according to claim 1 for further comprising monitoring compliance of the patient with the healthcare regime comprising:

i) providing information relating to the date, time and medication taken by the patient to the remote system by communicably linking the patient medication system to the remote system; and ii) communicating information relating to the date, time and status of the medication in the package to the remote system and comparing that information with the healthcare regime to determine compliance by the patient with the healthcare regime.

9. The method of claim 1 further comprising providing information from the remote system to the patient medication system to indicate whether the status of the patient medication system and/or identity of the patient corresponds with the information relating to the healthcare regime and/or the identity of patient.

10. The method of claim 1 further comprising registering other data relating directly or indirectly to the healthcare regime.

11. The method of claim 1 wherein the product comprises medication.

12. A method of providing an integrated healthcare management system for conducting a clinical trial which is interactive between at least one patient in the clinical trial and a party carrying out a clinical trial the system comprising:

i) registering a defined healthcare regime for the patient in a remote system;

ii) providing to the patient a patient medication system comprising:

a. a package comprising a product for dispensing and, information relating to the identity of the package; and b. an associated device with which the package is engagable so as to be readable by the associated device, the patient medication system being communicably linked to the remote system through the associated device;

iii) recording information relating to the identity of the package in the associated device or remote system whereby upon engagement of the package and the associated device, the recorded information is comparable with the information of the package to determine whether or not the information of the engaged package corresponds with the recorded information;

iv) recording information relating to the identity of the package in the patient medication system or remote system and whereby upon dispensing of the product said recorded information is comparable with the information of the package to determine whether or not the information of said package corresponds with said recorded information;

v. providing a unique identifier for the associated device and recording the identifier with the healthcare regime of the patient in the remote system to register the associated device;

vi. registering the patient with the associated device in the remote system;

vii. engaging the package of the patient medication system into the associated device;

viii. comparing the recorded information which relates to the identity of the package and which is stored in the associated device or remote system with the information of the package engaged with the associated device to determine whether or not the information of the engaged package corresponds with said recorded information;

ix. provided the information of the package corresponds to the stored information relating to the identity of the package, registering the package with the associated device in the remote system;

x. whereby information is provided to the remote system linking the package and associated device with the healthcare regime of the patient so as to enable authentication and registration of the medication package identity:

xi. providing to the party carrying out the clinical trial a communication port communicably linked to the remote system;

xii) periodically providing information relating to the identity of the patient and/or the status of the package from the patient medication system to the remote system;

xiii) comparing the information periodically transmitted to the remote system with the healthcare regime recorded for the patient in the remote system to ascertain whether the information corresponds with the recorded healthcare regime;

xiv) providing information from the remote system to the party carrying out the clinical trial indicating that a periodic transmission of information has been received by the remote system;

whereby the party carrying out the clinical trial may determine whether the patient has complied with the healthcare regime.

13. The method of claim 12 further comprising providing information from the remote system to the patient medication system to indicate whether the status of the patient medication system and/or identity of the patient corresponds with the information relating to the healthcare regime and/or the identity of patient.

14. The method of claim 12 further comprising registering other data relating directly or indirectly to the healthcare regime.

15. The method of claim 12 wherein the product comprises medication.

* * * * *